(12) United States Patent
Baell et al.

(10) Patent No.: US 7,507,839 B2
(45) Date of Patent: Mar. 24, 2009

(54) THERAPEUTIC ION CHANNEL BLOCKING AGENTS AND METHODS OF USE THEREOF

(75) Inventors: Jonathan B. Baell, Parkville (AU); Heike Wulff, Irvine, CA (US); Andrew J. Harvey, Parkville (AU); Raymond S. Norton, Parkville (AU); George K. Chandy, Irvine, CA (US)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 499 days.

(21) Appl. No.: 10/507,925

(22) PCT Filed: Mar. 20, 2003

(86) PCT No.: PCT/AU03/00351

§ 371 (c)(1), (2), (4) Date: Jul. 5, 2005

(87) PCT Pub. No.: WO03/078416

PCT Pub. Date: Sep. 25, 2003

(65) Prior Publication Data

US 2005/0261301 A1    Nov. 24, 2005

(30) Foreign Application Priority Data

Mar. 20, 2002 (AU) .................................... PS1272

(51) Int. Cl.
*C07D 307/00* (2006.01)
*A61K 31/34* (2006.01)

(52) U.S. Cl. ..................................... 549/462; 514/469
(58) Field of Classification Search ................ 546/196; 549/467, 462; 514/469
See application file for complete search history.

(56) References Cited

U.S. PATENT DOCUMENTS

| 3,862,176 A | 1/1975 | Fauran et al. |
| 4,753,965 A | 6/1988 | Stemerick et al. |
| 5,039,701 A | 8/1991 | Schlecker et al. |
| 5,494,895 A | 2/1996 | Garcia et al. |
| 6,051,590 A | 4/2000 | Bao et al. |
| 6,077,680 A | 6/2000 | Kem et al. |
| 6,355,805 B1 * | 3/2002 | Choi et al. .................. 546/301 |

FOREIGN PATENT DOCUMENTS

| WO | WO 97/16437 | 5/1997 |
| WO | WO 97/16438 | 5/1997 |

OTHER PUBLICATIONS

Wulff et al. The Physiologist 1999, 42, p. A-12.*
Wulff H. et al., "Nonpeptide Bivalent Blockers of Kv1.3 Channels Based on the Benzofuran Pharmacophore", *The Physiologist*, 42(A-12), Abstract 5.67 (1999).
Wulff H. et al., "Nonpeptide Bivalent Blockers of Kv1.3 Channels Based on the Benzofuran Pharmacophore", *Poster Abstract 1078 from Pharmaceutical Institute*, Kiel, Germany (1999).
Beeton C. et al., "Selective Blockade of T Lymphocyte K+ Channels Ameliorates Experimental Autoimmune Encephalomyelitis, a Model for Multiple Sclerosis", *Proc. Natl. Acad. Sci.* USA, 98(24):13942-13947 (2001).
Baell J.B. et al., "Khellinone Derivatives as Blockers of the Voltage-Gated Potassium Channel Kv1.3: Synthesis and Immunosuppressive Activity", *J. Med. Chem.*, 47:2326-2336 (2004).
Cianci J. et al., "Khellinone Derivatives as Blockers of the Kv1.3 Potassium Channel", *Poster Abstract for Connect 2005*, Sydney, Australia, (2005).
Baell J.B. et al., "Khellinone Derivatives as Blockers of the Kv1.3 Potassium Channel", *J. Med. Chem.*, 47:2326-2336 (2004).

* cited by examiner

*Primary Examiner*—D. Margaret Seaman
*Assistant Examiner*—Nizal S Chandrakumar
(74) *Attorney, Agent, or Firm*—Scully, Scott, Murphy & Presser, P.C.

(57) ABSTRACT

Various divalent ligands based on khellinone derivatives are described. These derivatives can be useful in the modulation of potassium channel activity in cells, including among others Kv1.3 channels found in T-cells. The compounds may also be useful in the treatment or prevention of autoimmune and inflammatory diseases, including multiple sclerosis.

4 Claims, No Drawings

THERAPEUTIC ION CHANNEL BLOCKING AGENTS AND METHODS OF USE THEREOF

FIELD OF THE INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Many autoimmune and chronic inflammatory diseases are related to immunoregulatory abnormalities. Diseases such as systemic lupus erythematosis, chronic rheumatoid arthritis, multiple sclerosis and psoriasis have in common the appearance of autoantibodies and self-reactive lymphocytes.

Multiple sclerosis is the most common neurological disease of young people. It is believed to cost more in medical care and lost income than any other neurological disease of young adults.

Multiple sclerosis affects the myelin sheaths of nerves. Myelin is an insulating material that coats most axons and allows rapid signal conduction over long distances by saltatory conduction. It is thought that antibodies and specialised cells of the immune system attack the myelin coating. This process leads to inflammation and scarring (sclerosis) which damages blood vessels in the area by the formation of a lesion known as a plaque. These plaques are characterised by being infiltrated by cells of the immune system. This results in demyelination with the consequential loss of the rapid signal conduction.

A possible method of treating these autoimmune and inflammatory diseases is by suppressing T-cell proliferation and modulating their activation.

The early stages of T-cell activation may be conceptually separated into pre-$Ca^{2+}$ and post-$Ca^{2+}$ events (Cahalan and Chandy 1997, *Curr. Opin. Biotechnol.* 8: 749). Following engagement of antigen with the T-cell antigen-receptor, activation of tyrosine kinases and the generation of inositol 1,4,5-triphosphate lead to the influx of $Ca^{2+}$ and the rise of cytoplasmic $Ca^{2+}$ concentration. The rise in $Ca^{2+}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{2+}$ signals while others require only a transient rise of $Ca^{2+}$. Furthermore, $Ca^{2+}$ immobilisation of the T-cell at the site of antigen presentation helps to cement the interaction between T-cell and the antigen-presenting cell and thereby facilitate local signalling between the cells.

Ion channels underlie the $Ca^{2+}$ signal of T-lymphocytes. $Ca^{2+}$ ions move across the plasma membrane through a channel termed the store-operated $Ca^{2+}$ channel or the calcium release-activated $Ca^{2+}$ channel. Two distinct types of potassium channels indirectly determine the driving force of calcium entry. The first is the voltage-gated Kv1.3 channel (Cahalan 1985, *J. Physiol.* 385: 197; Grissmer 1990, *Proc. Natl. Acad. Sci. USA* 87: 9411; Verheugen 1995, *J. Gen. Physiol.* 105: 765; Aiyar 1996, *J. Biol. Chem.* 271: 31013; Cahalan and Chandy 1997, *Curr. Opin. Biotechnol.* 8: 749) and the second is the intermediate-conductance calcium-activated potassium channel, IKCa1 (Grissmer 1993, *J. Gen. Physiol.* 102: 601; Fanger 1999 *J. Biol. Chem.* 274: 5746; Rauer 1999, *J. Biol. Chem.* 274: 21885; VanDorpe 1998, *J. Biol. Chem.* 273: 21542; Joiner 1997, *Proc. Natl. Acad. Sci. USA* 94: 11013; Khanna 1999, *J. Biol. Chem.* 274: 14838; Lodgson 1997, *J. Biol. Chem.* 272: 32723; Ghanshani 1998, *Genomics* 51: 160). When these potassium channels open, the resulting efflux of $K^+$ hyperpolarizes the membrane, which in turn accentuates the entry of $Ca^{2+}$, which is absolutely required for downstream activation events (Cahalan and Chandy 1997, *Curr. Opin. Biotechnol.* 8: 749).

The predominant voltage-gated channel in human T-lymphocytes is encoded by Kv1.3, a Shaker-related gene. Kv1.3 has been characterised extensively at the molecular and physiological level and plays a vital role in controlling T-lymphocyte proliferation, mainly by maintaining the resting membrane potential of resting T-lymphocytes. Inhibition of this channel depolarises the cell membrane sufficiently to decrease the influx of $Ca^{2+}$ and thereby prevents downstream activation events. Advantageously the homotetrameric Kv1.3 channel is almost exclusively located in T-lymphocytes.

Accordingly compounds which are selective Kv1.3 blockers are thus potential therapeutic agents as immunosuppressants for the prevention of graft rejection, and the treatment of autoimmune and inflammatory disorders. They could be used alone or in conjunction with other immunosuppressants, such as selective IKCa1 blockers or cyclosporin, in order to achieve synergism and/or to reduce toxicity, especially of cyclosporin.

U.S. Pat. No. 5,494,895 discloses the use of a thirty-nine amino acid peptide, scorpion peptide margatoxin, as a selective inhibitor and probe of Kv1.3 channels present in human lymphocytes, and also as an immunosuppressant. However the use of this compound is limited by its potent toxicity.

International Patent Application publication No.s WO 97/16438 and WO 091716437, and U.S. Pat. No. 6,051,590 describe the use of the triterpene, correolide and related compounds as immunosuppressants in the treatment of conditions in mammals affected or facilitated by Kv1.3 inhibition.

U.S. Pat. No. 6,077,680 describes DNA segments and proteins of derived from sea anemone species, more particularly ShK toxin from *Stichodactyla helianthus*. The ShK toxin was found to block Kv1.1, Kv1.3, Kv1.4 and Kv1.6, but a mutant ShK-K22DAP found to selectively block Kv1.3.

ShK toxin has recently been shown to both prevent and treat experimental autoimmune encephalomyelitis in Lewis rats, an animal model for human multiple sclerosis (Beeton 2001, et al., *Proc. Natl. Acad. Sci. USA* 98:13942), by selectively targeting T-cells chronically activated by the myelin antigen, MBP (myelin basic protein). The same study also Indicated that chronically activated encephalitogenic rat T-cells express a unique channel phenotype characterised by high expression of Kv1.3 channels (approximately 1500 per cell) and low numbers of IKCa1 channels (approximately 120 per cell). This channel phenotype is distinct from that seen in quiescent and acutely activated cells and may be a functionally relevant marker for chronically activated rat T lymphocytes.

Khellinone, a substituted benzofuran and natural product from certain plants, and 8-Methoxypsoralen (8-MOP), both commercially available products have been found to have blocking activity on the Kv1.3 channel.

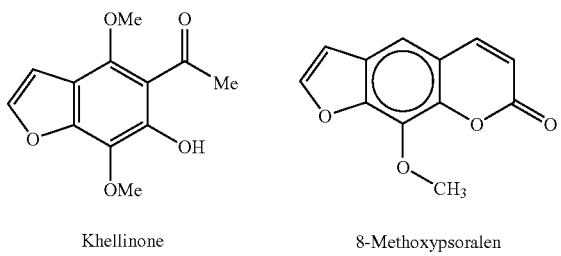

Khellinone          8-Methoxypsoralen

Khellinone, 8-MOP and four dimeric variants thereof were described in a Poster (abstract. No. 1078) at a meeting of the American Physiological Society in Snowmass, Colo. (*The Physiologist* 42: A12 (1999)). The authors were testing whether linking two active units with a spacer improved activity. Some of the bivalent derivatives were said to be ineffective, and others were said to block the Kv1.3 channel, but lack therapeutic utility due to their extreme sensitivity to hydrolysis (very poor stability) and high lipophilicity (poor solubility in clinical conditions).

SUMMARY OF THE INVENTION

In a first aspect the invention relates to compounds of the general formula I

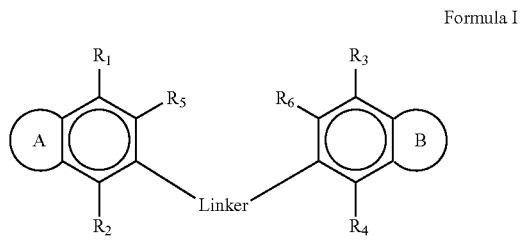

Formula I wherein $R_1$, $R_2$, $R_3$ and $R_4$ are independently selected from H, OH, optionally substituted alkyl, optionally substituted alkoxy, optionally substituted alkenyl, optionally substituted alkynyl, optionally substituted haloalkyl, optionally substituted cycloalkyl, optionally substituted aryl, optionally substituted arylalkyl, optionally substituted cycloalkylalkyl, cyano, halo, alkoxycarbonyl, alkyl carbonyloxy, alkylamido, nitro and alkylamino;

Linker is a divalent spacer group that provides a spacing between the two aromatic rings to which it is joined of from 6 to 11 atoms when measured across the shortest route between the two aromatic rings;

A and B are fused rings independently selected from optionally substituted 5- to 7-membered aromatic, heteroaromatic and non-aromatic heterocyclic rings;

$R_5$ and $R_6$ are independently selected from —C(O)$R_7$, —C(N$R_7$)$R_7$ and —C(S)$R_7$, wherein each $R_7$ is independently selected from hydrogen, an alkyl group, an alkoxy group and an hydroxy group;

or a salt or pharmaceutically acceptable derivative thereof;
with the proviso that at least one of $R_1$, $R_2$, $R_3$, or $R_4$ is not a methoxy group when $R_5$ and $R_6$ are —C(O)CH$_3$, rings A and B are unsubstituted furyl and Linker is —O—CH$_2$—C$_6$H$_4$—CH$_2$—O—.

In a second aspect, the present invention provides a pharmaceutical composition for use as an immunosuppressant, the composition comprising an effective amount of compound of Formula I, a product thereof, or a pharmaceutically acceptable derivative thereof, and optionally a carrier or diluent.

In a third aspect, the present invention provides a method of preventing or treating of autoimmune or chronic inflammatory diseases, the prevention of rejection of foreign organ transplants and/or related afflictions, diseases and illnesses by the administration of a compound of formula I or a pharmaceutically acceptable derivative thereof, or a composition containing a compound of formula I or a pharmaceutically acceptable derivative thereof.

In a fourth aspect, the present invention provides a method of modulating potassium ion channel activity of T-cells by the application of a compound of Formula I, or a pharmaceutically acceptable derivative thereof, to said T-cells.

In a fifth aspect, the present invention provides the use of a compound of formula I, or a pharmaceutically acceptable derivative thereof, in the manufacture of a medicament for the treatment or prevention of autoimmune or chronic inflammatory disease, or the prevention of rejection of foreign organ transplants and/or related afflictions.

DETAILED DESCRIPTION OF THE INVENTION

The present invention is predicated on the discovery that, contrary to the teaching of the prior art, bivalent ligand systems can be quite stable. In addition it has been found the clinical solubility, Kv1.3 channel selectivity and/or activity of bivalent ligand systems compounds may be enhanced over that of the previously taught bivalent ligand systems.

Whilst it has been suggested that a possible method of increasing the activity of compounds at a receptor site is to link two active compounds via a suitable linker to create a bivalent ligand (Portoghese, P. S., *Trends in Pharmacological Sciences*, 1989, 10, 230-235), the known experiments with some Kv1.3 channel active compounds have largely been unsuccessful. Ideally local concentration effects should increase the activity of the bivalent ligands by a factor substantially greater than two.

Unfortunately, a number of unpredictable factors appear to influence the success of this approach including whether linker joining the two active compounds permits the bridging of two neighbouring binding sites, the surface morphology of the region around the binding sites and chemical and structural affects of modifying the active compound by adding a linker group. Furthermore, even if these criteria are met, and the divalent ligand has significantly enhanced binding to the target protein Kv1.3, when compared to the monovalent ligand, poor physicochemical properties such as poor aqueous solubility can render any such divalent ligand of no therapeutic use.

However, it is believed that the compounds of the invention may address one or more of these problems and thus may be more selective and/or active and/or soluble than the known divalent ligands, in addition to having good stability.

With respect to the present invention there is a Linker joined to two ligands, in order to provide the compound of formula I, as earlier described. The "Linker" is a divalent spacer group that provides a space between the two aromatic rings to which it is joined of from 6 to 11 atoms when measured across the shortest route between the two aromatic rings (the bridging portion). Ideally this length should permit the active components to bridge two neighbouring binding sites.

Examples of suitable divalent spacer groups include optionally substituted alkylene groups having from 6 to 11 carbon atoms when measured across the shortest route between the two aromatic rings. One or more of the methylene (—CH$_2$—) groups in the bridging portion may be replaced with heteroatoms, such as O, S or NR$^a$ wherein R$^a$ is selected from hydrogen and lower alkyl. One or more of the methylene (—CH$_2$—) groups in the bridging portion may also be replaced with atoms forming part of an optionally substituted ring such as one or more optionally substituted aromatic ring or optionally substituted non aromatic ring(s). The rings may include one or more heteroatoms selected from O, S and N. The ring heteroatoms may form part of the bridging portion.

The bridging portion (including non-aromatic ring(s) forming part of the bridging portion) may include one or more unsaturated sites. An unsaturated site occurs when an ethylene moiety (—CH$_2$CH$_2$—) has been replaced with —CH=CH— or —C≡C—.

The spacer group may be optionally substituted by a wide range of substituents, such as those described below with reference to the definition of 'optionally substituted'. By way of a non-limiting example, the spacer group may be optionally substituted with one of more substituents selected from hydroxy, optionally substituted alkyl, optionally substituted alkoxy, optionally substituted alkenyl, optionally substituted alkynyl, haloalkyl, optionally substituted cycloalkyl, optionally substituted aryl, optionally substituted arylalkyl, optionally substituted cycloalkylalkyl, cyano, halo, alkoxycarbonyl, alkylcarbonyloxy, alkylamido, nitro and alkylamino.

The Linker may optionally include one or more aromatic, heteroaromatic or non aromatic rings. For example the Linker may include aryl or cyclohexane rings. The included ring(s), preferably a phenyl ring, may constitute two or more of the atoms that form the shortest path between the two aromatic rings linked by the Linker.

Preferably the Linker is a divalent moiety of the form —X—(CH$_2$)$_n$—X—, where each X is the same or different and is selected from O, S and NR$^a$ (where R$^a$ is independently hydrogen or lower alkyl), preferably O, and n is a integer of from 4 to 9, and preferably of from 6 to 8, and one or more of the methylene groups may be optionally substituted and may optionally include one or more unsaturated sites.

Another preferred linker is a divalent moiety of the form —X—(CH$_2$)$_p$—Y—(CH$_2$)$_q$—X—, where each X is the same or different and is selected from O, S and NR$^a$ (where R$^a$ is independently hydrogen or lower alkyl), preferably O, and p and q are integer numbers equal to or greater than 1, one or more of the methylene groups may be optionally substituted and —(CH$_2$)$_p$— and —(CH$_2$)$_q$— may include one or more unsaturated sites, Y is selected from divalent moieties such as an optionally substituted aromatic ring such as phenyl; —S—S—; —C(O)—; —C(O)O—; —NR$^b$C(O)— wherein R$^b$ is hydrogen or lower alkyl; or —O—. When Y is a phenyl group it may be optionally substituted, and is preferably substituted with one or more polar substituents, such as —C(O)OR$^c$[OR$^c$]$_n$ wherein each R$^c$ is independently hydrogen or a lower alkyl and n is a integer from 0 to 10.

In this specification unless otherwise defined "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkoxyamino, alkenyloxy, aryloxy, benzyloxy, haloalkoxy, haloalkenyloxy, haloaryloxy, cyano, carboxyl, nitro, amino, alkylamino, dialkylamino, alkenylamino, alkynylamino, arylamino, diarylamino, benzylamino, acyl, alkenylacyl, alkynylacyl, arylacyl, acylamino, heterocyclyl, heterocycloxy, heterocylamino, haloheterocyclyl, carboalkoxy, carboaryloxy, alkylthio, alkylsulfonyl, alkylsulfinyl, benzylthio, sulphonamido, —C(O)NRR', —NR—C(S)NR'R", —NRC(O)OR, —NRC(O)NR'R", —NRC(O)R', —C(=NR)NR'R", —C(=NR'R")SR, —C(S)NR'R", —C(S)NR'R", —C(=NCN)—NR'R", —NR—C(=NCN)SR, —NR"SO$_2$R, —NR'C(S)R, —NR'C(O)R and —NRSO$_2$CF$_3$, where R, R' and R" are hydrogen or lower alkyl.

Where the optional substituent includes an aromatic or heterocyclic aromatic ring, that ring may be substituted with one or more groups selected from alkyl, alkenyl, alkynyl, halo, haloalkyl, haloalkenyl, haloalkynyl, hydroxy, alkoxy and alkenyloxy.

The term "alkyl" as used alone or in combination herein refers to a straight or branched chain saturated hydrocarbon group containing from one to ten carbon atoms and the terms "C$_{1-6}$ alkyl" and "lower alkyl" refer to such groups containing from one to six carbon atoms, such as methyl ("Me"), ethyl ("Et"), n-propyl, isopropyl, n-butyl, isobutyl, sec-butyl, tert-butyl and the like.

The term "alkenyl" means a two to ten carbon, straight or branched hydrocarbon containing one or more double bonds, preferably one or two double bonds.

Examples of alkenyl include ethenylene, propenylene, 1,3-butadienyl, and 1,3,5-hexatrienyl.

The term "alkynyl" means a two to ten carbon, straight or branched hydrocarbon containing one or more triple bonds, preferably one or two triple bonds.

The term "alkoxy" as used alone or in combination herein refers to a straight or branched chain alkyl group covalently bound via an O linkage and the terms "C$_{1-6}$ alkoxy" and "lower alkoxy" refer to such groups containing from one to six carbon atoms, such as methoxy, ethoxy, propoxy, isopropoxy, butoxy, t-butoxy and the like.

The term "aromatic" or "aryl" when used alone or in combination refers to an unsubstituted or optionally substituted monocyclic or bicyclic aromatic hydrocarbon ring system. Preferred aromatic ring systems are optionally substituted phenyl ("Ph") or naphthalenyl groups.

Preferably, the aromatic or aryl group is phenyl and may be optionally substituted with up to four but more usually with one or two groups, preferably selected from C$_{1-6}$ alkyl, C$_{1-6}$ alkoxy, cyano, trifluoromethyl and halo.

When the aromatic group is optionally substituted by alkoxycarbonyl, the alkoxy group may itself be optionally substituted by one or more alkoxy groups which themselves may be further optionally substituted. Thus the aromatic group can be substituted with a moiety such as —C(O)OR[OR]$_n$ wherein R is a lower alkyl group and n is a integer from 0 to 10.

The term "heteroaromatic" group as used herein refers to a stable, aromatic monocyclic or polycyclic ring system containing carbon atoms and other atoms selected from nitrogen, sulfur and/or oxygen.

Preferably, a heteroaromatic group is a 5 or 6-membered monocyclic ring (optionally benzofused) or an 8-11 membered bicyclic ring which consists of carbon atoms and contains one, two, or three heteroatoms selected from nitrogen, oxygen and/or sulfur.

Examples of preferred heteroaromatic groups are isoxazolyl, imidazolyl, thiazolyl, isothiazolyl, pyridyl, furyl, pyrimidinyl, pyrazolyl, pyridazinyl, furazanyl and thienyl. The heteroaryl group may be attached to the parent structure through a carbon atom or through any heteroatom of the heteroaryl that results in a stable structure.

The terms "halo" and "halogen" as used herein to identify substituent moieties, represent fluorine, chlorine, bromine or iodine, preferably chlorine or fluorine.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" includes pharmaceutically acceptable esters, prodrugs, solvates and hydrates, and pharmaceutically acceptable addition salts of the compounds or the derivatives. Pharmaceutically acceptable derivatives may include any pharmaceutically acceptable salt, hydrate or any other compound or prodrug which, upon administration to a subject, is capable of providing (directly or indirectly) a compound of formula I or an antivirally active metabolite or residue thereof.

The pharmaceutically acceptable salts include acid addition salts, base addition salts, salts of pharmaceutically acceptable esters and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicyclic, sulfamic, or tartartic acids. The counter ion of quarternary amines and pyridiniums include chloride, bromide, iodide, sulfate, phosphate, methansulfonate, citrate, acetate, malonate, fumarate, sulfamate, and tartate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

It will be appreciated that compound of formula I and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms and all isomeric forms of the compounds being included in the present invention. In some preferred embodiments of the invention, and with reference to the general formula I the following preferred definitions apply:

$R_1$, $R_2$, $R_3$ and $R_4$ are independently selected from H, OH, nitro, cyano, halo, optionally substituted alkyl, optionally substituted cycloalkyl, optionally substituted alkenyl, optionally substituted alkoxy, optionally substituted alkynyl, optionally substituted haloalkyl, optionally substituted cycloalkyl, optionally substituted aryl, optionally substituted aryloxy, optionally substituted heteroaryloxy, optionally substituted arylalkyl, optionally substituted alkoxycarbonyl, optionally substituted alkylcarbonyloxy, optionally substituted arylcarbonyloxy, optionally substituted alkylamido and optionally substituted alkylamino;

Rings A and B are optionally substituted and are independently selected from isoxazolyl, oxazolyl, imidazolyl, thiazolyl, isothiazolyl, pyridinyl, furyl, pyrimidinyl, pyrazolyl, pyrrolyl, pyridazinyl, furyl and thiophenyl rings, more preferably from thiophenyl, furyl and pyrrolyl;

$R_5$ is —$COR_7$, and each $R_7$ is independently selected from hydrogen, an alkyl and an alkoxy group, more preferably each $R_7$ is independently a lower alkyl group and most preferable a methyl group;

The Linker is an optionally substituted divalent moiety of the form —X—$(CH_2)_n$—X—, where each X is the same or different and is selected from O, S and $NR^a$ (each $R^a$ is independently selected from hydrogen and lower alkyl, preferably hydrogen), X preferably being O, and n is a integer between 4 and 9, and —$(CH_2)_n$— may include one or more unsaturated sites.

Alternatively, the Linker is a divalent moiety of the form —X—$(CH_2)_p$—Y—$(CH_2)_q$—X—, where each X is the same or different and is selected from O, S and $NR^a$, where each $R^a$ is independently selected from hydrogen and lower alkyl, X preferably being O, and p and q are integer numbers equal to or greater than 1, one or more of the methylene groups may be optionally substituted and —$(CH_2)_p$— and —$(CH_2)_q$— may include one or more unsaturated sites and Y is selected from an optionally substituted aromatic ring (such as phenyl), —S—S—, —N(lower alkyl)-CO— and —O—. When Y is a phenyl ring, it is preferable to substitute it with a polar group such as —$C(O)OR^c[OR^c]_n$ wherein each $R^c$ is independently hydrogen or lower alkyl and n is a integer from 0 to 10.

A preferred embodiment of this aspect of the invention is a compound of Formula II:

Formula II

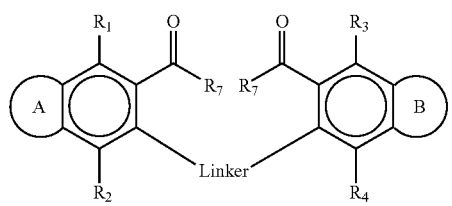

wherein $R_1$, $R_2$, $R_3$, $R_4$, linker, A and B are as described above and each $R_7$ is independently selected from an alkyl or alkoxy group, with the proviso that at least one of $R_1$, $R_2$, $R_3$, or $R_4$ is not a methoxy group when $R_5$ and $R_6$ are —C(O)CH$_3$, rings A and B are unsubstituted furyl and Linker is —O—CH$_2$—C$_6$H$_4$—CH$_2$—O—.

A more preferred embodiment of this aspect of the invention is a compound of the Formula IIIa or IIIb.

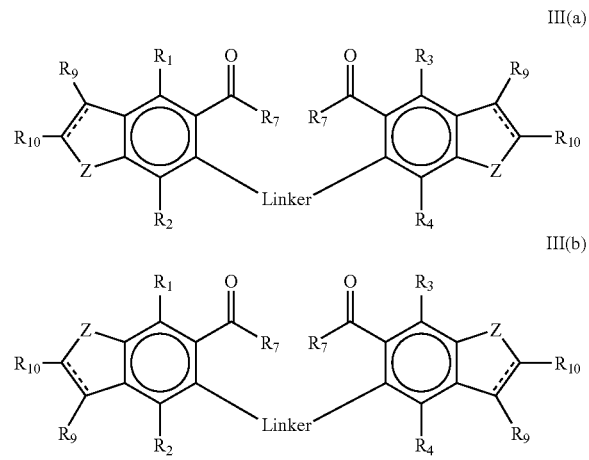

III(a)

III(b)

wherein $R_1$, $R_2$, $R_3$, $R_4$, $R_7$ and Linker are as described above for formula II, and each Z is independently a heteroatom such as O, S, NH or N(loweralkyl), preferably O, and each $R_9$ and $R_{10}$ are independently selected from H, OH, optionally substituted alkyl, optionally substituted alkoxy, optionally substituted alkenyl, optionally substituted alkynyl, optionally substituted haloalkyl, optionally substituted cycloalkyl, optionally substituted aryl, optionally substituted arylalkyl, optionally substituted cycloalkylalkyl, cyano, halo, alkoxycarbonyl, alkyl carbonyloxy, alkylamido, nitro and alkylamino, and the dashed lines represent optionally present bonds, with the proviso that at least one of $R_1$, $R_2$, $R_3$, or $R_4$ is not a methoxy group when $R_7$ are both CH$_3$, each $R_9$ and $R_{10}$ are hydrogen, each Z is O, the dashed lines represents bonds and Linker is —O—CH$_2$—C$_6$H$_4$—CH$_2$—O—.

A more preferred embodiment of this aspect of the invention is a compound of the Formula IV Formula IV

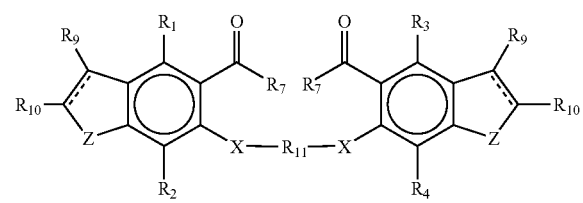

wherein $R_1$, $R_2$, $R_3$, $R_4$, $R_7$, $R_9$, $R_{10}$, Z and the dashed lines are as described above for formula IIIa and IIIb, and each X is independently a heteroatom selected from S, O NH and N(lower alkyl) and $R_{11}$ is a divalent group having from 4 to 9 atoms along the shortest distance between the heteroatoms X to which it is attached, with the proviso that at least one of $R_1$, $R_2$, $R_3$, or $R_4$ is not a methoxy group when each $R_7$ is CH$_3$, each Z is O, each $R_9$ and $R_{10}$ is hydrogen, each X is O and $R_{11}$ is —CH$_2$—C$_6$H$_4$—CH$_2$—.

The divalent group $R_{11}$ may be selected from a wide range of groups including optionally substituted alkylene groups of from 4 to 9 carbon atoms across the shortest distance between the X's. The alkylene group may have one or more double or triple bonds. One or more of the optionally substituted methylene groups can be replaced with heteroatoms, such as O, S or NR$^a$ wherein R$^a$ is selected from hydrogen or lower alkyl. One or more of the methylene groups may be replaced with atoms forming part of a ring structure; such as an optionally substituted aromatic ring and optionally substituted aliphatic ring. The ring may include unsaturated sites and which may include one or more heteroatoms selected from O, S and N.

Preferably $R_{11}$ a divalent moiety of the form —(CH$_2$)$_n$—, where n is an integer of from 4 to 9, and one or more of the methylene groups may be optionally substituted and —(CH$_2$)$_n$— may include one or more unsaturated sites.

Alternatively $R_{11}$ is a divalent moiety of the form —(CH$_2$)$_p$—Y—(CH$_2$)$_q$—, p and q are integer numbers equal to or greater than 1, one or more of the methylene groups may be optionally substituted and —(CH$_2$)$_p$— and —(CH$_2$)$_q$— may include one or more unsaturated sites and Y is selected from an optionally substituted aromatic group such as phenyl, —S—S—, —NR$^b$CO— or —O—, where R$^b$ is hydrogen or lower alkyl. When Y is a phenyl group it is preferable to substitute it with a polar group such as —C(O)OR$^c$[OR$^c$]$_n$ wherein each R$^c$ is independently hydrogen or lower alkyl and n is a integer from 0 to 10.

A more preferred embodiment of this aspect of the invention is a compound of the Formula V.

Formula V

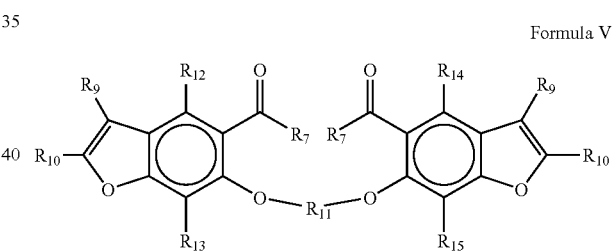

wherein each $R_7$, $R_9$, $R_{10}$ and $R_{11}$ are as described above, and $R_{12}$ and $R_{14}$ are independently selected from H, OH, cyano, halo, nitro and an optional substituted group selected from alkyl, alkenyl, alkoxy, optionally substituted alkynyl, haloalkyl, cycloalkyl, aryl, arylalkyl, cycloalkyl alkyl, alkoxycarbonyl, alkylcarbonyloxy, alkylamido and alkylamino;

$R_{13}$ and $R_{15}$ are independently selected from H, OH, and an optionally substituted group selected from alkyl, alkoxy, aryloxy, heteroaryloxy, alkylcarbonyloxy and arylcarbonyloxy;

with the proviso that at least one of $R_{12}$, $R_{13}$, $R_{14}$ and $R_{15}$ is not methoxy when $R_7$ is methyl, $R_9$ and $R_{10}$ are H, and $R_{11}$ is —CH$_2$C$_6$H$_4$CH$_2$—.

A more preferred embodiment of this aspect of the invention is a compound of the Formula VI

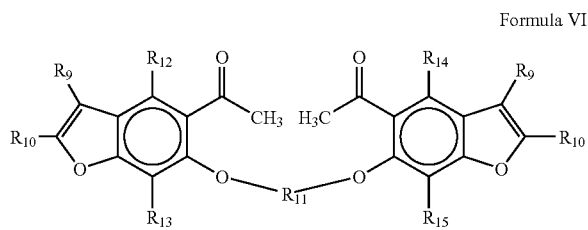

Formula VI wherein each $R_9$, $R_{10}$, $R_{11}$, $R_{12}$, $R_{13}$, $R_{14}$ and $R_{15}$ are as described above.

More preferably, each $R_9$ and $R_{10}$ is H or optionally substituted alkyl, $R_{11}$ is an optionally substituted moiety of the formula —$(CH_2)_n$—, where n is 4, 5, 6 or 7, or an optionally substituted moiety of the formula —$CH_2$—$C_6H_4$—$CH_2$—, and each $R_{12}$ and $R_{13}$ are optionally substituted alkyloxy, preferably lower alkyloxy, groups.

Most preferably the compounds are:—
1,5-bis(5-acetyl-4,7-dimethoxybenzofuran-6-yloxy)pentane;
1,6-bis(5-acetyl-4,7-dimethoxybenzofuran-6-yloxy)hexane;
1,4-bis(5-acetyl-4,7-dimethoxybenzofuran-6-yloxy)butane;
1,4-bis(5-acetyl-4-methoxybenzofuran-6-yloxymethyl)benzene;
di-(5-acetyl-4-methoxybenzofuran-6-yloxyethyl)ether;
1,4-bis(5-acetyl-4-methoxybenzofuran-6-yloxymethyl)benzoic acid;
1,4-bis(5-acetyl-4-methoxybenzofuran-6-yloxymethyl)benzoic acid methyl ester;
1,4-bis(5-acetyl-4-methoxybenzofuran-6-yloxymethyl)benzoic acid, tetraethyleneglycol monomethyl ether ester;
5-acetyl-4,7-dimethoxybenzofuran-6-yloxyethanethiol, disulfide dimer;
1,6-bis(5-acetyl-4,7-dimethoxybenzofuran-6-yloxy)-N-methyl-3-aza-4-oxohexane;
2,5-bis(5-acetyl-4,7-dimethoxybenzofuran-6-yloxymethyl)furan;
2,4-bis(5-acetyl-4,7-dimethoxybenzofuran-6-yloxymethyl)furan;
2,5-bis(5-acetyl-4,7-dimethoxybenzofuran-6-yloxymethyl)thiophene;
2,4-bis(5-acetyl-4,7-dimethoxybenzofuran-6-yloxymethyl)thiophene;
2,5-bis(5-acetyl-4,7-dimethoxybenzofuran-6-yloxymethyl)thiazole;
2,4-bis(5-acetyl-4,7-dimethoxybenzofuran-6-yloxymethyl)thiazole;
2,5-bis(5-acetyl-4,7-dimethoxybenzofuran-6-yloxymethyl)thiadiazole;
1,4-bis(5-acetyl-4,7-dimethoxybenzofuran-6-yloxymethyl)cyclopentane;
2,5-bis(5-acetyl-4,7-dimethoxybenzofuran-6-yloxymethyl)tetrahydrofuran;
2,5-bis(5-acetyl-4,7-dimethoxybenzofuran-6-yloxymethyl)tetrahydrothiophene;
1,4-bis(5-acetyl-4,7-dimethoxybenzofuran-6-yloxymethyl)-2-hydroxybenzene;
2,5-bis(5-acetyl-4,7-dimethoxybenzofuran-6-yloxymethyl)pyridine;
2,5-bis(5-acetyl-4,7-dimethoxybenzofuran-6-yloxymethyl)pyrimidine;
2,5-bis(5-acetyl-4,7-dimethoxybenzofuran-6-yloxymethyl)pyrazine;
3,6-bis(5-acetyl-4,7-dimethoxybenzofuran-6-yloxymethyl)pyridazine;
2,6-bis(5-acetyl-4,7-dimethoxybenzofuran-6-yloxymethyl)pyridine;
2,6-bis(5-acetyl-4,7-dimethoxybenzofuran-6-yloxymethyl)pyrimidine;
2,6-bis(5-acetyl-4,7-dimethoxybenzofuran-6-yloxymethyl)pyridazine;
2,4-bis(5-acetyl-4,7-dimethoxybenzofuran-6-yloxymethyl)pyridine;
4,6-bis(5-acetyl-4,7-dimethoxybenzofuran-6-yloxymethyl)pyrimidine;
3,5-bis(5-acetyl-4,7-dimethoxybenzofuran-6-yloxymethyl)pyridine;
3,5-bis(5-acetyl-4,7-dimethoxybenzofuran-6-yloxymethyl)pyridazine;
1,5-bis(5-acetyl-4,7-dimethoxybenzofuran-6-ylthio)pentane;
1,6-bis(5-acetyl-4,7-dimethoxybenzofuran-6-ylthio)hexane;
1,4-bis(5-acetyl-4,7-dimethoxybenzofuran-6-ylthio)butane;
1,4-bis(5-acetyl-4-methoxybenzofuran-6-ylthiomethyl)benzene;
1,5-bis(5-acetyl-4,7-dimethoxybenzofuran-6-ylamino)pentane;
1,6-bis(5-acetyl-4,7-dimethoxybenzofuran-6-ylamino)hexane;
1,4-bis(5-acetyl-4,7-dimethoxybenzofuran-6-ylamino)butane; and
1,4-bis(5-acetyl-4-methoxybenzofuran-6-yloxyamino)benzene.

The invention also includes where possible a salt or pharmaceutically acceptable derivative such as a pharmaceutically acceptable salt, ester, solvate and/or prodrug of the above mentioned embodiments of the first aspect of the invention.

In the second aspect, the present invention provides a pharmaceutical compositions for use as an immunosuppressant, the composition comprising an effective amount of compound of Formula I, or a pharmaceutically acceptable derivative thereof, and optionally a carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of compound of Formula I administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The compositions may further contain one or more other immunosuppressive compounds. For example the compositions may contain a second immunosuppressive agent such as azathioprine, brequinar sodium, deoxyspergualin, mizaribine, mycophenolic acid morpholino ester, cyclosporin, FK-506 and rapamycin.

The compounds of the present invention may be useful in the therapeutic or prophylactic treatment of the resistance to transplantation of organs or tissue (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases; rheumatoid arthritis, systemic lupus erythematosus, nephrotic syndrome lupus, Palmo-planter pustulosis, Hashimoto's thyroiditis, multiple sclerosis, Guillain-Barre syndrome, myasthenia gravis, type I diabetes uveitis, juvenile-onset or recent-onset diabetes mellitus, diabetic neuropathy, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T-cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Sjoegren's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Berger's disease, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and anti-inflammatory activity; and treatment of immunodepression or a disorder involving immunodepression, including AIDS, cancer, senile dementia, trauma, chronic bacterial infection, type II diabetes mellitus as glucose-dependent insulin secretagogues, cardiac arrhythmias such as atrial or ventricular fibrillation, epilepsy, muscular fasciculations, urinary incontinence, certain central nervous system disorders via modulating neural conduction or neurotransmitter release.

For certain of the abovementioned conditions it is clear that the compounds may be used prophylactically as well as for the alleviation of acute symptoms.

References herein to "treatment" or the like are to be understood to include such prophylactic treatment, as well as treatment of acute conditions.

It is envisaged that the compounds may be particularly useful in the treatment of multiple sclerosis. This chronic neurological disorder affects the nerves in central nervous system. As earlier discussed normally most nerves in the body are insulated by a protective sheath of fatty substance called myelin. Multiple sclerosis causes demyelination, in which this protective sheath becomes inflamed and ultimately destroyed.

By modulating or changing the immune system response that is thought to be responsible for the attack on the central nervous system it should be possible to attack the cause of the disease itself, rather than the more traditional method of controlling the symptoms.

The nature of the disease is such that it may be possible to control multiple sclerosis without unduly suppressing the patient's immune system. Based on the earlier discussed chronically activated rat T-lymphocytes study, it is speculated that multiple sclerosis may be a product of chronically activated T-cells having a channel phenotype characterised by high expression of Kv1.3 channels and low numbers of IKCa1 channels. As this channel phenotype is distinct from that seen in quiescent and acutely activated cells it may provide a useful means for controlling multiple sclerosis without the significant side effects of less specific drugs.

Furthermore, in demyelinating diseases such as multiple sclerosis or diabetic neuropathy, the destruction of the myelin sheath evokes an internodal potassium current in myelinated nerve fibers by uncovering normally silent potassium channels. These abnormal potassium currents contribute to the conduction failure observed in demyelinated neurons. Blockers of axonal potassium channels such as the unselective compound 4-aminopyridine (4-AP) have been demonstrated to overcome conduction failure in vitro and to improve disability in certain multiple sclerosis patients. 4-AP (Fampridine) is currently in clinical trials for multiple sclerosis. Compounds that block both the Kv1.3 channel in autoreactive T-cells and the Kv1.1-Kv1.2 heteromultimeric channels present in the Ranvier Nodes of myelinated nerves might be ideally suited the treatment of multiple sclerosis. Such compounds could simultaneously enhance impulse propagation in demyelinated neurons and modify the immune response.

Thus in a third aspect, the invention provides a method of preventing or treating of autoimmune or chronic inflammatory diseases, the prevention of rejection of foreign organ transplants and/or related afflictions, by the administration of a compound of formula I or a composition containing the compound or a pharmaceutically acceptable derivative thereof.

Accordingly in a preferred form of the invention, there is provided a means for controlling multiple sclerosis by the application of a blocker of the Kv1.3 channel, preferably a selective channel blocker of the Kv1.3 channel, and optionally also a blocker of Kv1.1 and/or Kv1.2 channels, by the application of a compound of formula I or composition containing the compound of formula I.

In a fourth aspect, the invention provides a method of modulating potassium ion channel activity of T-cells by the application of a compound of Formula I to said T cells. Preferably the compounds of the invention inhibit the potassium ion channel activity of T-cells.

Preferably the potassium channel activity inhibited by the compound of Formula I is a voltage-gated potassium channel, for example, Kv1.1-Kv1.7. More preferably the potassium ion channel activity is the voltage-gated potassium channel, Kv1.3 of a T-cell. Preferably the compound selectively inhibits the Kv1.3 channel, and optionally also the Kv1.1 and/or Kv1.2 channels.

In a fifth aspect, the invention there is provided a process for the production of the compounds of Formula I.

Dimeric compounds of the Formula V or VI, preferred forms of Formula I, are readily made from khellinone and a suitable linking compound. Khellinone is a preferred starting material as it is a natural product from plants which is cheap and commercially available. The linking compound acts as the source of the bivalent group $R_{11}$ and together with the two oxygens to which it is attached provided a bivalent Linker group of Formula I.

The preferred reaction is a straightforward alkylation and takes place through the attack by the phenolate oxygen of khellinone, induced by base, on the electrophilic carbon atoms adjacent to halogen atoms in a (bishalo)alkane:

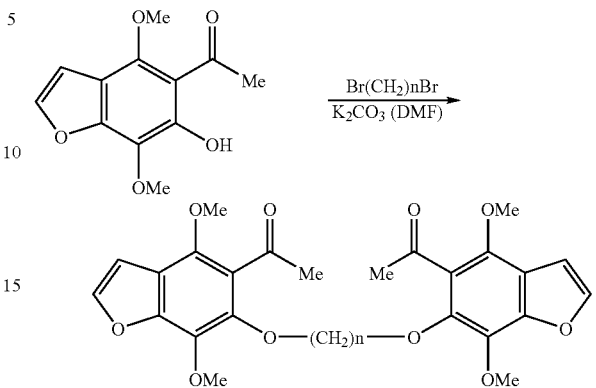

For example, when bisbromopentane is used as the linking compound with Khellinone, the reaction produces Khellinone dimers having pentane linkage:—

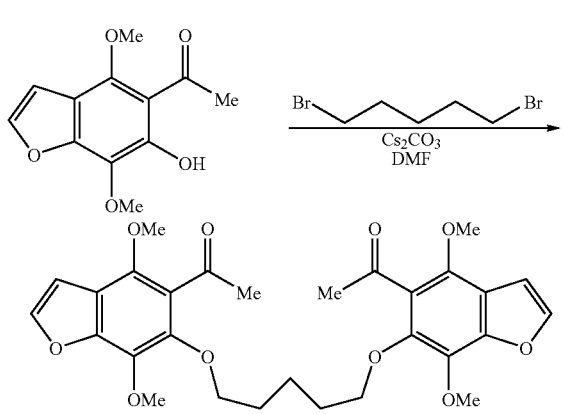

Variations of this reaction include first modifying khellinone to create a derivative thereof by adding, removing or modifying one or more of the functional groups attached to the ring system. For example, the methoxy groups could be selectively manipulated to provide to higher alkyl derivatives of khellinone and used in the above scheme as precursors for dimer formation.

Another starting material is Khellin, which can be regarded as a protected khellinone. This compound could be bis-demethylated with boron tribromide and the resulting hydroquinone selectively alkylated, by the use of a weaker base such as $K_2CO_3$ to alkylate only the non-hydrogen bonded phenol, followed by a stronger base such as $Cs_2CO_3$ to alkylate the hydrogen-bonded phenolic OH (hydrogen bond shown as dotted line), as shown.

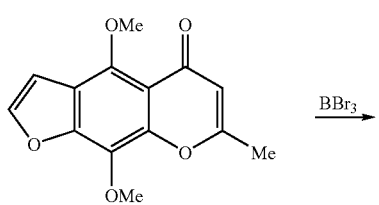

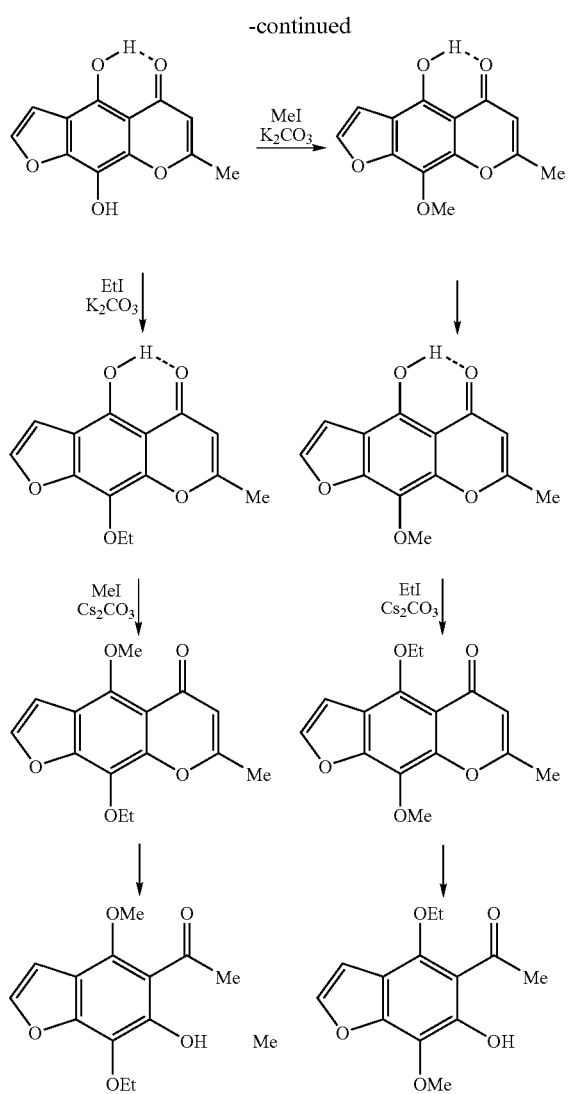

Another variation is to add, remove or modify the substituents of the dimeric product to form new derivatives. This could be achieved by using standard techniques for functional group inter-conversion, well known in the industry such as those described in Comprehensive organic transformations: a guide to functional group preparations by Larock R C, New York, VCH Publishers, Inc. 1989.

Examples of functional group inter-conversions are: —C(O)NRR' from —CO$_2$CH$_3$ by heating with or without catalytic metal cyanide, e.g. NaCN, and HNRR' in CH$_3$OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR'" with H$_3$NR$^+$OAc$^-$ by heating in alcohol; —C(NR'R")SR from —C(S)NR'R" with R—I in an inert solvent, e.g. acetone; —C(S)NR'R" (where R' or R" is not hydrogen) from —C(S)NH$_2$ with HNR'R"; —C(=NCN)—NR'R" from —C(=NR'R")—SR with NH$_2$CN by heating in anhydrous alcohol, alternatively from —C(=NH)—NR'R" by treatment with BrCN and NaOEt in EtOH; —NR—C(=NCN)SR from —NHR' by treatment with (RS)$_2$C=NCN; —NR" SO$_2$R from —NHR' by treatment with ClSO$_2$R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR' with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R' from RC(O)R' by R"CO$_3$H; —CCH$_2$OH from —C(O)OR' with Na/R'OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH.

Another variation is to use different linking compounds. Preferably the linker compound is of the general formula L-R$_{11}$-L, where L is a suitable leaving group, such as halogen, more preferably Br, and R$_{11}$, is a moiety as earlier described including —(CH$_2$)$_n$— or —(CH$_2$)$_p$—Y—(CH$_2$)$_q$—, where n, Y, p and q are as earlier described. R$_{11}$ may optionally include one or more unsaturated sites and may be optionally substituted.

Examples of linking compounds include:

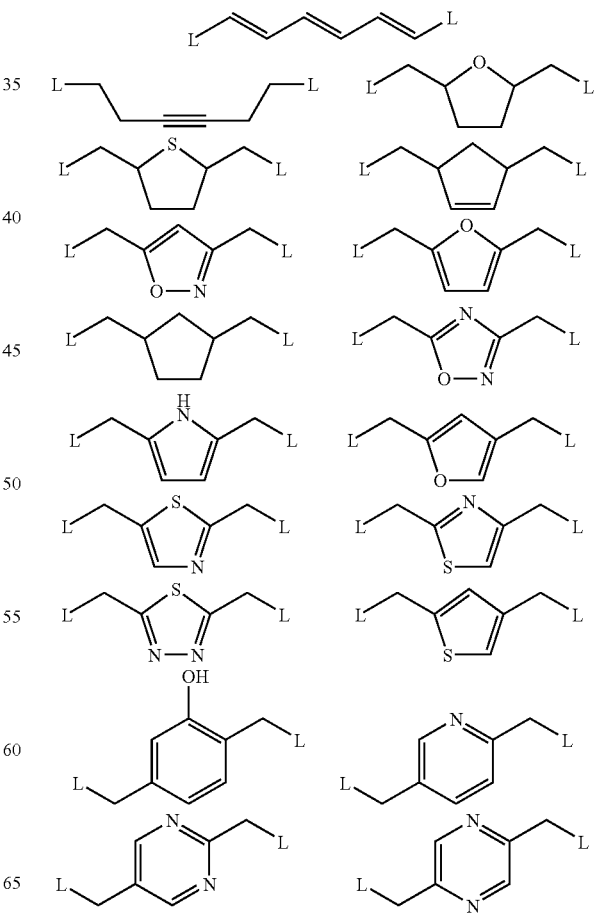

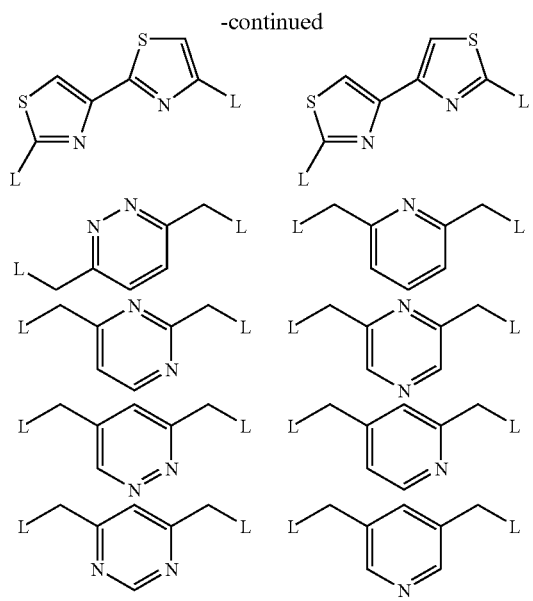

Preferably L is chlorine or bromine. These linker compounds can be used in much the same way as the earlier reaction with bishaloalkane. An example scheme is set out below.

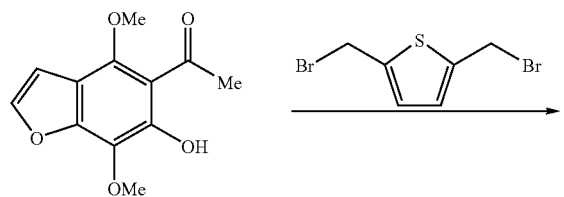

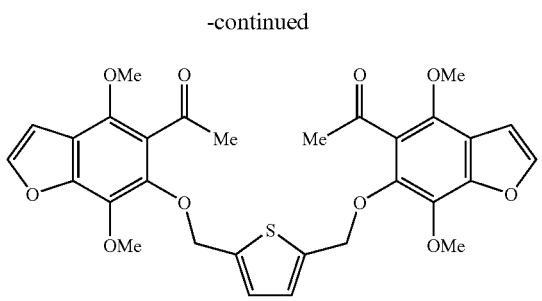

The linking compounds may need to be modified before the linking reaction. The nitrogen atoms of heterocyclic rings may need to be protected during the linking reaction. The nitrogen atoms could be protected as by their reversible conversion to an N-oxide form. Likewise, a phenolic hydroxy group in the linker would need to be protected during the link reaction. Suitable protecting groups are well known in industry and have been described in many references such as Protecting Groups in Organic Synthesis, Greene T W, Wiley-Interscience, New York, 1981.

The production of compounds of the invention having a "Linker" which is joined to the two aromatic rings by a nitrogen or sulphur requires a different strategy. When starting with khellinone, the ketone group should be protected. A dithiol-based protection strategy is shown in the example below, although other strategies may be used. The phenolic OH should be converted to a leaving group by, for example, tosylation as shown. This compound could then be reacted with an amine-based or thiol-based bis-nucleophile, to give the resulting dimer as shown, after unmasking of the ketone group.

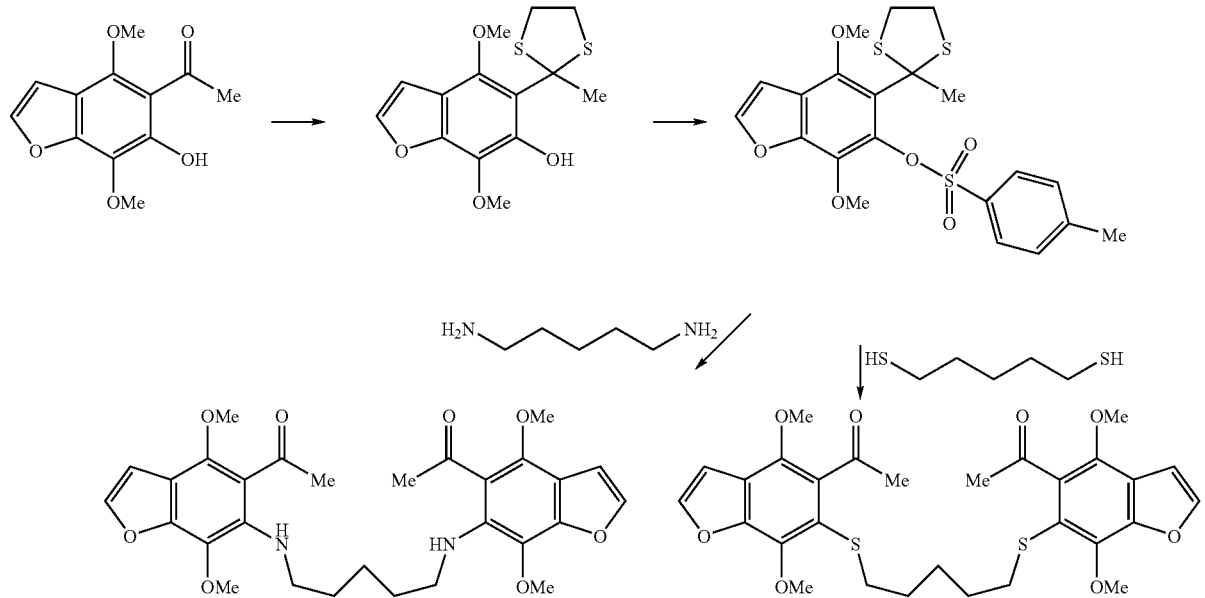

Variations of this reaction could be used to provide other compounds of formula I to VI.

Yet another variation is the formation of heterodimeric (also known as non-homodimeric) compounds. One end of the linking compound may be protected with a suitable protecting group before the initial reaction with khellinone or a derivative thereof. The protecting group could be removed and the resultant compound reacted with a different khellinone derivative.

Alternatively two or more different khellinone derivatives may be mixed together and subsequently reacted with a linker compound in basic conditions to form a mixture of products that are then separated or used in combination.

In order that the present invention may be more readily understood, we provide the following non-limiting examples.

EXAMPLES

General Procedure

To a suspension of the benzofuran (1.0 mmol) and cesium carbonate (1.0 mmol) in N,N-dimethylformamide ("DMF") (2 mL) under nitrogen was added the dibromide (0.5 mmol) and the reaction mixture was stirred at 55° C. for 16 h. The reaction mixture was diluted with ethyl acetate (10 mL) and washed with 10% citric acid solution (3×10 mL) and brine (10 mL) and dried ($MgSO_4$) and concentrated in vacuo. The resulting residue was purified by flash chromatography.

Example 1

1,5-bis[(5-acetyl-4,7-dimethoxybenzofuran-6-yloxy)])pentane

The compound was prepared from khellinone and 1,5-dibromopentane according to the General Procedure. Purification by flash chromatography eluting with ethyl acetate/cyclohexane (1:9 to 2:8) afforded the product (177 mg, 65%) as a grey oil.

MS (ES): 541 (M+H)$^+$, 563 (M+Na)$^+$; $^1$H NMR ($CDCl_3$) δ 1.57 (2H, m), 1.77 (4H, tt, J=7.0, 7.0 Hz), 2.51 (6H, s), 3.95 (6H, s), 4.08 (10H, m), 6.84 (2H, d, J=2.1 Hz), 7.54 (2H, d, J=2.1 Hz). $^{13}$C NMR ($CDCl_3$) δ 22.2 ($CH_2$), 29.7 ($CH_2$), 32.7 ($CH_3$), 61.0 ($CH_3$), 61.1 ($CH_3$), 74.9 ($CH_2$), 104.9 (CH), 116.3 (C), 124.5 (C), 134.4 (C), 143.9 (C), 144.4 (CH), 144.7 (C), 148.6 (C), 201.8 (C).

Example 2

1,6-bis[(5-acetyl-4,7-dimethoxybenzofuran-yloxy)])hexane

The compound was prepared from khellinone and 1,6-dibromohexane according to the General Procedure. Purification by flash chromatography eluting with ethyl acetate/cyclohexane (1:9 to 2:8) afforded the product (215 mg, 77%) as a colourless solid.

An analytical sample was prepared by recrystallisation from ethyl acetate/cyclohexane:

Anal. calcd for $C_{30}H_{34}O_{10}$, C, 65.0, H, 6.2; found C, 64.9, H, 6.1; MS (ES): 555 (M+H)$^+$, 577 (M+Na)$^+$; mp 89-90° C. $^1$H NMR ($CDCl_3$) δ 1.48 (4H, m), 1.75 (4H, m), 2.52 (6H, s), 3.97 (6H, s), 4.06 (10H, m), 6.85 (2H, d, J=2.4 Hz), 7.55 (2H, d, J=2.4 Hz). $^{13}$C NMR ($CDCl_3$) δ 25.6 ($CH_2$), 26.8 ($CH_2$), 32.7 ($CH_3$), 61.0 ($CH_3$), 61.2 ($CH_3$), 75.1 ($CH_2$), 104.9 (CH), 116.3 (C), 124.5 (C), 134.4 (C), 143.9 (C), 144.4 (CH), 144.8 (C), 148.6 (C), 201.8 (C).

Example 3

1,4-(bis[(5-acetyl-4,7-dimethoxybenzofuran-6-yloxy)])butane

The compound was prepared from khellinone and 1,4-dibromobutane according to the General Procedure. Purification by flash chromatography eluting with ethyl acetate/cyclohexane (3:7) afforded the product (221 mg, 84%) as white needles.

MS (ES): 527 (M+H)$^+$, 549 (M+Na)$^+$; mp 119-120° C. $^1$H NMR ($CDCl_3$) δ 1.87 (4H, m), 2.50 (6H, s), 3.95 (6H, s), 4.06 (6H, s), 4.09 (4H, m), 6.83 (2H, d, J=2.1 Hz), 7.54 (2H, d, J=2.1 Hz). $^{13}$C NMR ($CDCl_3$) δ 26.6 ($CH_2$), 32.7 ($CH_3$), 61.0 ($CH_3$), 61.1 ($CH_3$), 74.7 ($CH_2$), 104.9 (CH), 116.3 (C), 124.5 (C), 134.4 (C), 143.9 (C), 144.4 (CH), 144.6 (C), 148.6 (C), 201.8 (C).

Example 4

1,4-bis(5-acetyl-4-methoxybenzofuran-6-yloxymethyl)benzene

The compound was prepared from visnaginone and α,α'-dibromo-p-xylene according to the General Procedure. Purification by flash chromatography eluting with ethyl acetate/cyclohexane (1:9 to 2:8) afforded the product (20 mg, 8%) as a white solid:

Anal. calcd for $C_{30}H_{26}O_8$, C, 70.0, H, 5.1; found C, 70.1, H, 5.1; MS (thermospray, LC/MS): 515 (M+H)$^+$, 532 (M+$NH_4^+$); mp-196-197° C. $^1$H NMR ($CDCl_3$) δ 2.51 (6H, s), 4.05 (6H, s), 5.10 (4H, s), 6.80 (2H, s), 6.86 (2H, d, J=2.3 Hz), 7.40 (4H, s), 7.49 (2H, d, J=2.3 Hz). $^{13}$C NMR compound insufficiently soluble in dimethyl sulfoxide ("DMSO") for $^{13}$C NMR analysis.

Example 5

Di-(5-acetyl-4,7-dimethoxybenzofuran-6-yloxyethyl)])ether

To a suspension of khellinone (236 mg, 1.0 mmol) and anhydrous potassium carbonate (138 mg, 1.0 mmol) in DMF (2 mL) under nitrogen was added (2-bromoethyl)ether (63 μL, 0.5 mmol) and the reaction mixture was stirred at room temperature for 2 days. The reaction mixture was diluted with ethyl acetate (10 mL) and washed with 10% citric acid solution (3×10 mL) then brine (10 mL) and dried ($MgSO_4$) and concentrated in vacuo. The resulting residue was purified by flash chromatography eluting with ethyl acetate/cyclohexane (1:9 to 3:7) to afford the product (99 mg, 37%) as a colourless oil.

MS (ES): 543 (M+H)$^+$, 565 (M+Na)$^+$. $^1$H NMR ($CDCl_3$) δ 2.53 (6H, s), 3.77 (4H, t, J=4.8 Hz), 3.96 (6H, s), 4.06 (6H, s), 4.24 (6H, t, J=4.8 Hz), 6.85 (2H, d, J=2.1 Hz), 7.55 (2H, d, J=2.1 Hz). $^3$C NMR ($CDCl_3$) δ 32.7 ($CH_3$), 61.0 ($CH_3$), 61.2 ($CH_3$), 70.0 ($CH_2$), 73.7 ($CH_2$), 104.9 (CH), 116.5 (C), 124.5 (C), 134.3 (C), 144.0 (C), 144.5 (CH), 144.8 (C), 148.6 (C), 201.7 (C).

Example 6

2,5-Bis(5-acetyl-4,7-dimethoxybenzofuran-6-yloxymethyl)benzoic acid, tetraethyleneglycol monomethylether ester To a suspension of the methyl ester (80 mg, 0.13 mmol) in tetraethyleneglycol monomethylether (720 μL, 3.80 mmol) was added titanium (IV) isopropoxide (12 μL, 0.042 mmol)

and the reaction mixture was stirred under nitrogen at 100° C. for six hours. After this period the reaction was incomplete by TLC and further titanium (IV) isopropoxide (25 µL, 0.085 mmol) was added and the reaction mixture was stirred at 100° C. for eight hours. The reaction was quenched with 1M HCl (1 mL) and then the reaction mixture was partitioned over 1M HCl/ethyl acetate (1:1, 120 mL). The organic phase was washed with saturated sodium bicarbonate (60 mL) then dried (MgSO$_4$) and concentrated in vacuo. The resulting residue was purified by flash chromatography eluting with ethyl acetate/petroleum ether (3:2) to afford the starting material methyl ester (30 mg). Further elution with ethyl acetate/petroleum ether (7:3) furnished the desired product (32 mg, 50% by returned starting material) as a colourless oil.

MS (ES): 826 (M+NH$_4^+$). $^1$H NMR (CDCl$_3$) δ 2.49 (3H, s), 2.49 (3H, s), 3.35 (3H, s), 3.51 (2H, m), 3.58-3.68 (12H, m), 3.81 (2H, t, J=4.8 Hz), 3.99 (3H, s), 4.00 (3H, s), 4.03 (3H, s), 4.11 (3H, s), 4.44 (2H, t, J=4.8 Hz), 5.12 (2H, s), 5.56 (2H, s), 6.88 (1H, d, J=2.1 Hz), 6.90 (1H, d, J=2.1 Hz), 7.59 (1H, d, J=2.1 Hz), 7.61 (1H, d, J=2.1 Hz), 7.67 (1H, d, J=8.1 Hz), 7.86 (1H, d, 8.1 Hz), 8.09 (1H, s). $^{13}$C NMR (CDCl$_3$) δ 32.7 (CH$_3$), 32.7 (CH$_3$), 58.9 (CH$_3$), 61.1 (CH$_3$), 61.1 (CH$_3$), 61.3 (CH$_3$), 61.3 (CH$_3$), 63.5 (CH$_2$), 69.0 (CH$_2$), 70.4 (CH$_2$), 70.5 (CH$_2$), 71.8 (CH$_2$), 74.2 (CH$_2$), 76.0 (CH$_2$), 104.9 (CH), 105.0 (CH), 116.6 (C), 116.7 (C), 124.6 (C), 124.6 (C), 127.4 (C), 127.5 (CH), 130.3 (CH), 132.3 (CH), 134.4 (C), 134.6 (C), 136.2 (C), 139.9 (C), 144.0 (C), 144.1 (C), 144.4 (C), 144.5 (CH), 144.6 (CH), 148.5 (C), 148.7 (C), 166.4 (C), 201.5 (C), 201.7 (C).

Example 7

2,5-Bis(5-acetyl-4,7-dimethoxy-6-benzofuran-6-yloxymethyl)benzoic acid, methyl ester The compound was prepared from khellinone (147 mg, 0.62 mmol) and 2,5-di(bromomethyl)benzoate methyl ester (100 mg, 0.31 mmol) according to the General Procedure. Purification by flash chromatography eluting with ethyl acetate/cyclohexane (1:4 to 2:3) afforded the product (149 mg, 76%) as a straw-coloured solid.

MS (ES): 633 (M+H)$^+$, 650 (M+NH$_4^+$); mp 87-89° C. $^1$H NMR (CDCl$_3$) δ 2.48 (3H, s), 2.48 (3H, s), 3.87 (3H, s), 3.98 (3H, s), 3.99 (3H, s), 4.03 (3H, s), 4.09 (3H, s), 5.11 (2H, s), 5.55 (2H, s), 6.87 (1H, d, J=2.7 Hz), 6.88 (1H, d, J=2.7 Hz), 7.57 (1H, d, J=2.7 Hz), 7.59 (1H, d, J=2.7 Hz), 7.67 (1H, dd, J=1.5, 8.1 Hz), 7.85 (1H, d, 8.1 Hz), 8.07 (1H, d, 1.5 Hz). $^{13}$C NMR (CDCl$_3$) δ 32.7 (CH$_3$), 32.7 (CH$_3$), 51.9 (CH$_3$), 61.1 (CH$_3$), 61.1 (CH$_3$), 61.2 (CH$_3$), 61.2 (CH$_3$), 74.1 (CH$_2$), 76.0 (CH$_2$), 104.9 (CH), 105.0 (CH), 116.6 (C), 116.7 (C), 124.3 (C), 124.5 (C), 127.5 (C), 127.7 (CH), 130.2 (CH), 132.2 (CH), 134.3 (C), 134.5 (C), 136.2 (C), 139.7 (C), 144.0 (C), 144.1 (C), 144.4 (CH), 144.5 (CH), 144.6 (C), 144.6 (C), 148.5 (C), 148.7 (C), 166.9 (C), 201.5 (C), 201.7 (C).

Example 8

2,5-Bis(5-acetyl-4,7-dimethoxybenzofuran-6-yloxymethyl)benzoic acid

Step (i) Synthesis of 2,5-di(bromomethyl)benzoate methyl ester intermediate

To a solution of 2,5-dimethylbenzoate methyl ester (328 mg, 2.0 mmol) in carbon tetrachloride (10 mL) was added N-bromosuccinimide (890 mg, 5.0 mmol) and AIBN (2,2'-azobisisobutyronitrile, 16 mg, 0.1 mmol) and the reaction mixture was heated at reflux for 4 h. The resulting suspension was filtered and the residue was washed with chloroform (3×5 mL). The pooled organics were concentrated in vacuo to give a mixture of product and succinimide by $^1$H NMR. The mixture was dissolved into dichloromethane (20 mL) and washed with water (2×10 mL). The dichloromethane phase was dried (MgSO$_4$) and concentrated in vacuo and the resulting residue was purified by flash chromatography eluting with 2% ether in petroleum ether to furnish the product (0.50 g, 78%) as a white solid. An analytical sample was prepared by recrystallisation from methanol.

mp 79.5-80° C.; lit. mp (MeOH) 81-83° C. $^1$H NMR (CDCl$_3$) δ 3.98 (3H, s), 4.49 (2H, s), 4.94 (2H, s), 7.46 (1H, d, J=7.8 Hz), 7.53 (1H, dd, J=1.8, 7.8 Hz), 8.00 (1H, d, J=1.8 Hz).

Step (ii): synthesis of 2,5-Bis(5-acetyl-4,7-dimethoxybenzofuran-6-yloxymethyl)benzoic acid To a solution of the methyl ester of step (i) (63 mg, 0.10 mmol) in tetrahydrofuran ("THF") (3 mL) was added 0.25 M lithium hydroxide in methanol/water (2:1, 3 mL) and the reaction mixture was stirred at 80° C. for 16 h. The reaction was incomplete by TLC thus lithium hydroxide (42 mg, 1.0 mmol) was added and the suspension was stirred at 90° C. for 16 h. The reaction mixture was concentrated to one third volume and then diluted with water (10 mL) and extracted with ether (15 mL). The aqueous phase was ice-cooled and acidified to pH4 (by Universal Indicator) with 1M HCl. Extraction with ethyl acetate (2×20 mL) and subsequent washing of the pooled organics with brine (10 mL) followed by drying (MgSO$_4$) and evaporation afforded a residue that was purified by flash chromatography eluting with 3% methanol in dichloromethane. The desired acid was obtained (26 mg, 42%) as a colourless oil.

Anal. calcd for C$_{33}$H$_{30}$O$_{12}$, C, 64.1, H, 4.9; found C, 63.8, H, 5.2. $^1$H NMR (d$_6$-acetone) δ 2.43 (3H, s), 2.44 (3H, s), 4.01 (3H, s), 4.01 (3H, s), 4.03 (3H, s), 4.15 (3H, s), 5.23 (2H, s), 5.60 (2H, s), 7.13 (1H, d, J=2.4 Hz), 7.13 (1H, d, J=2.4 Hz), 7.75 (1H, dd, J=1.8, 7.8 Hz), 7.86 (1H, d, J=2.4 Hz), 7.86 (1H, d, J=2.4 Hz), 7.91 (1H, d, J=7.8 Hz), 8.18 (1H, d, J=1.8 Hz). $^{13}$C NMR (d$_6$-acetone) δ 31.9 (CH$_3$), 31.9 (CH$_3$), 60.4 (CH$_3$), 60.5 (CH$_3$), 60.5 (CH$_3$), 60.6 (CH$_3$), 74.1 (CH$_2$), 75.6 (CH$_2$), 105.1 (CH), 105.1 (CH), 116.6 (C), 116.7 (C), 124.6 (C), 124.6 (C), 127.0 (CH), 127.4 (C), 130.3 (CH), 131.9 (CH), 135.4 (C), 135.6 (C), 136.6 (C), 139.9 (C), 144.4 (C), 144.5 (C), 145.2 (CH), 149.4 (C), 167.2 (C), 204.1 (C), 204.2 (C).

Example 9

Biological Activity

The effectiveness of the generated compounds in blocking the Kv1.3 current was assayed on L929 cells stably expressing mKv1.3 or on activated human T cells. The generation of this cell line has been previously described (Grissmer et al. (1995) *Mol. Pharmacol.* 45: 1227). The cells were grown in Dulbecco's modified Eagle's medium containing 10% fetal calf serum, 2 mM L-glutamine, 1 mM Na$^+$ pyruvate, 100 units/ml penicillin, 100 µg/ml streptomycin and 250 µg G418 (to keep them under selection pressure). The cells were studied in the whole-cell configuration of the patch-clamp technique. The holding potential in all experiments was −80 mV. Currents were recorded in normal Ringer solution (160 mM NaCl, 4.5 mM KCl, 2 mM CaCl$_2$, 1 mM MgCl$_2$, 10 mM HEPES, pH 7.4, 290-310 mOsm) with an internal pipette solution containing 134 mM KF, 2 mM MgCl$_2$, 10 mM HEPES, 10 mM EGTA (pH 7.2, 290-310 mOsm). If currents exceeded 2 nA 60-80% series resistance compensation was used. 200-ms depolarising pulses to 40 mV were applied every 30 s (Grissmer at al. (1995) *Mol. Pharmacol.* 45: 1227). Each compound was tested twice at two different concentrations. $K_d$ values were determined by fitting the reduction of the normalized peak current to the Hill equation.

The doses that have a half-maximal effect on the Kv1.3 current for a range of comparative compounds and compounds of the invention tested for binding to Kv1.3 are depicted below in Table 1. Physical data is provided where available.

Those compounds less active at Kv1.3 are of interest as being potentially selective for Kv channels other than Kv1.3.

TABLE 1

Biological data

| Example | Structure | Physical data | $K_d$ (channel type) |
|---|---|---|---|
| Comparative Example 1 (Khellinone) | 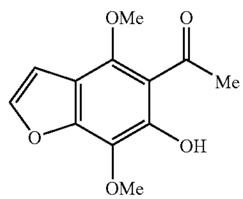 | | 70 μM (Kv$_{1.3}$) |
| Comparative Example 2 (3-MOP) | 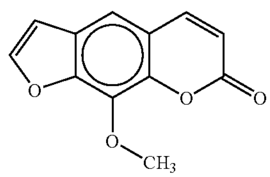 | | 160 μM (Kv$_{1.3}$) |
| Comparative Example 3 | 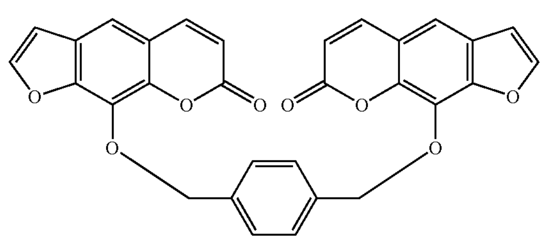 | | 17 μM (Kv$_{1.3}$) |
| Comparative Example 4 | 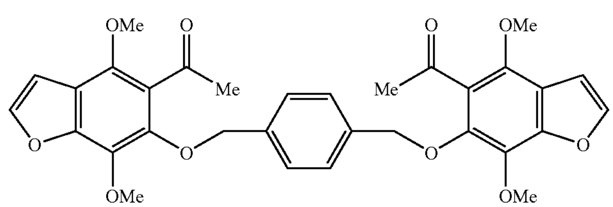 | mw574 colourless solid; m.p. 192° C. | 3 μM (Kv$_{1.1}$) 5 μM (Kv$_{1.2}$) 0.28 μM (Kv$_{1.3}$) 2.2 μM (Kv$_{1.4}$) 1.1 μM (Kv$_{1.5}$) >20 μM (IKCa1) No effect at 10 μM (SKMI) |
| Comparative Example 5 | 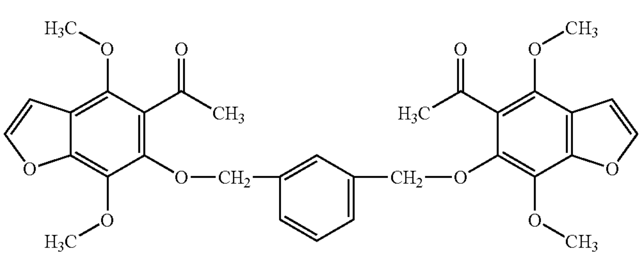 | mw 574 colourless solid; m.p. 112° C. | 0.56 μM (Kv$_{1.3}$) |

TABLE 1-continued

Biological data

| Example | Structure | Physical data | $K_d$ (channel type) |
|---|---|---|---|
| Comparative Example 6 | 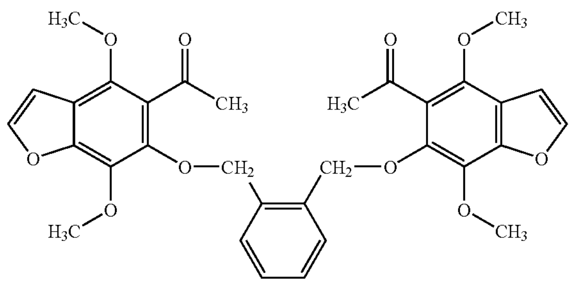 | mw 574 colourless solid; m.p. 140° C. | 7 μM ($Kv_{1.3}$) |
| Example 1 | 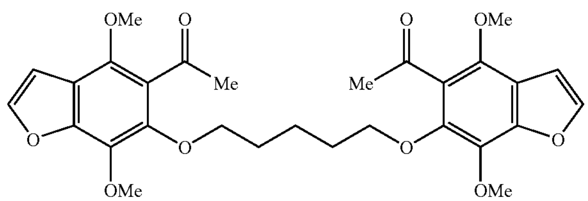 | mw 540 colourless oil | 0.82 μM ($Kv_{1.3}$) 1.5 μM ($Kv_{1.2}$) |
| Example 2 | 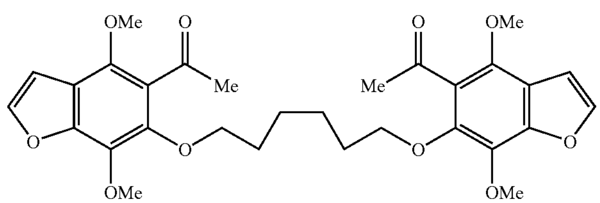 | mw 554 colourless solid; m.p. 89–90° C. | 0.68 μM ($Kv_{1.3}$) Block phasic 0.32 μM ($Kv_{1.1}$) 0.25 μM ($Kv_{1.2}$) |
| Example 3 | 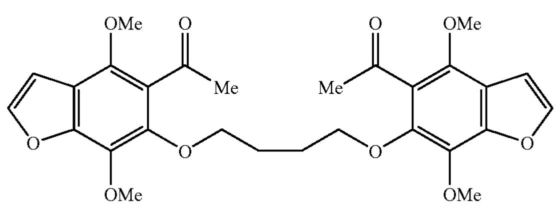 | mw 526 colourless needles; m.p. 117° C. | 3.5 μM ($Kv_{1.3}$) |
| Example 4 | 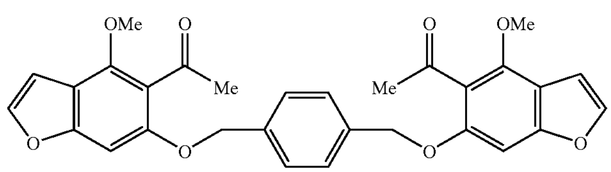 | mw 514 colourless solid; mp 196–197° C. | 1.1 μM ($Kv_{1.3}$) No effect at 5 μM ($Kv_{1.2}$) |
| Example 5 | 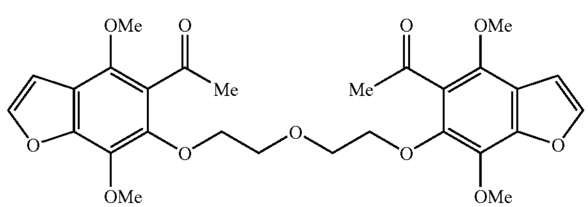 | mw 542 colourless oil | 4 μM ($Kv_{1.3}$) |

TABLE 1-continued

Biological data

| Example | Structure | Physical data | $K_d$ (channel type) |
|---|---|---|---|
| Example 6 | 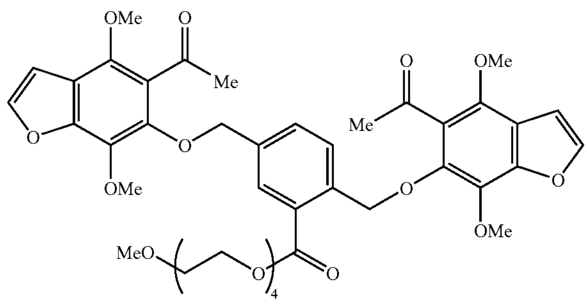 | mw 809 brown oil | |
| Example 7 | 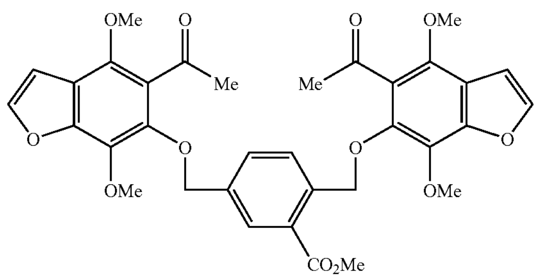 | mw 632 tan solid; m.p. 87–89° C. | 3 μM ($Kv_{1.3}$) |
| Example 8 | 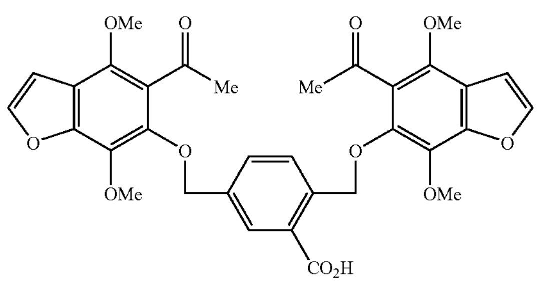 | mw 618 yellow oil | 5 μM ($Kv_{1.3}$) |
| Example 9 | 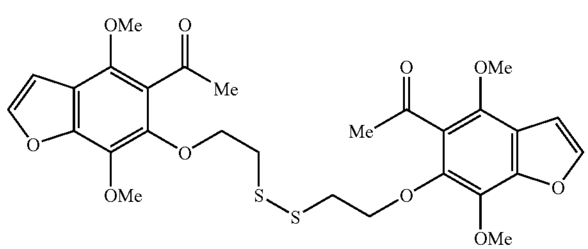 | | |
| Example 10 | 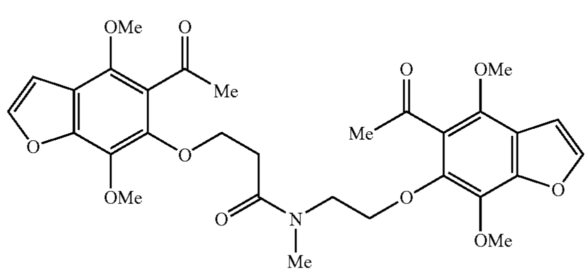 | | |

In the case of known comparative example 4, it was found that this compound was so poorly soluble in aqueous media, it could not be tested for inhibition of T-cell proliferation in a cell-based assay. The comparative example 4 was thus considered to lack therapeutically use. However, the compound was surprisingly found to have good stability.

Given the poor solubility of comparative example 4, it was surprisingly found that examples 1 and 2 were soluble enough in aqueous media to be tested for inhibition of T-cell proliferation in a cell-based assay. This was unexpected given the lipophilicity of these compounds. The n-butyl fragment in example 2 is considerably more lipophilic than the phenyl group located in the equivalent position of comparative example 4 (fragment hydrophobicity value 2.5 verses 1.9 respectively).

It is thought that the improvement in aqueous solubility relates to the crystalline structure of the compounds. The Linker in example 2 is similar in length to the length of the Linker in comparative example 4, and as such it may permit similar binding of the non-linker portions to Kv1.3. However, the Linker of example 2 should have greater conformational flexibility relative to the more rigid phenyl-based linker in comparative example 4. This may have produced a compound which is inherently much less crystalline than that of the comparative example. The fact that the melting point of comparative example 4 is more than twice that of example 2 lends support to this theory.

Example 5 is also significantly more soluble in aqueous conditions than comparative example 2. It has a lower melting point, and is an oil at room temperature. The oxygen atom midway in the Linker, being polar, may further increase water solubility, though the placement of this atom appears to have caused some weakening in the binding to Kv1.3, as indicated by the decreased $K_d$ value.

Examples 6 to 8 are believed to provide improved solubility by the inclusion of a substituent in the ortho position of the phenyl ring of the Linker. Ortho substitution can decrease the crystallinity of some organic compounds. It is speculated that example 8 is not even a solid because of the ortho effect, despite the inclusion of a carboxylic acid substituent which is generally regarded as an inherently "crystalline" group. The solubility may have been further improved by the use of polar groups as the ortho substituent on the phenyl ring.

Example 10 may be more soluble and more active due to the inclusion of a cis-amide bond. This may be firmly projecting the benzofuran binding groups in a manner similar to comparative example 4, whilst providing reduced lipophilicity due to the presence of a polar N-methyl amide group.

[$^3$H]—Thymidine Incorporation Assay

[$^3$H]-thymidine incorporation is a widely used test to assay the proliferative activity of human and rodent lymphocytes. As cells divide [$^3$H]-thymidine will be incorporated into the newly synthesised DNA of the resulting daughter cells. The faster cells grow the more radioactive [$^3$H]-thymidine will be incorporated. Any compound that inhibits lymphocytes proliferation will reduce the uptake of radioactivity by the cells treated with it compared to the untreated controls.

Example 2 was tested to determine its ability to inhibit [H]-thymidine incorporation. Resting peripheral blood mononuclear cells from healthy volunteers were seeded at 2×10$^5$ cells per well in medium (RPMI 1640 supplemented 10% fetal calf serum, 2 mM glutamine, 1 mM sodium pyruvate, 1% nonessential amino acids, 100 units/ml penicillin, 100 μg/ml streptomycin and 50 μM β-mercaptoethanol) in flat-bottom 96 well plates (final volume 200 μl). Cells were pre-incubated with the compound of example 2 for 60 min, and were stimulated with 5 ng/ml anti-CD3 Ab) for 48 h. [$^3$H]-Thymidine (1 μCi per well) was added for the last 6 h. Cells were harvested onto glass fibre filters and radioactivity measured in a scintillation counter. All experiments were done in triplicate. Results are reported below in Table 2 as normalised for maximum [$^3$H]-thymidine incorporation for controls. Example 2 was found to be potently antiproliferative, with an EC$_{50}$ of approximately 800 nM.

TABLE 2

| [$^3$H]-thymidine incorporation | |
|---|---|
| Concentration compound 2 | Normalised [3H]-TdR incorporation |
| 0 (untreated control) | 1 |
| 100 nM | 0.86 +/− 0.04 |
| 250 nM | 0.76 +/− 0.06 |
| 1 μM | 0.38 +/− 0.05 |
| 10 μM | 0.01 +/− 0.003 |

EC$_{50}$ approximately 800 nM

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A compound of Formula I

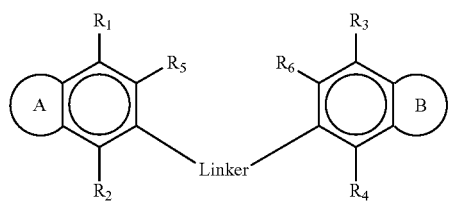

or a pharmaceutically acceptable salt thereof,
wherein R$_1$, R$_2$, R$_3$ and R$_4$ are OCH$_3$;
Linker is O—(CH$_2$)$_n$—O, wherein n is an integer of from 4, 5, 6, 7, 8 or 9;
A and B are fused furan rings; and
R$_5$ and R$_6$ are both C(O)CH$_3$;
wherein the linker and the benzofuran oxygen have a meta relationship.

2. The compound according to claim 1 selected from
1,5-bis(5-acetyl-4,7-dimethoxybenzofuran-6-yloxy)pentane;
1,6-bis(5-acetyl-4,7-dimethoxybenzofuran-6-yloxy)hexane; and
1,4-bis(5-acetyl-4,7-dimethoxybenzofuran-6-yloxy)butane.

3. A pharmaceutical composition comprising an effective amount of the compound of claim 1, or a pharmaceutically acceptable salt thereof, in association with a pharmaceutically acceptable carrier or diluent.

4. A pharmaceutical composition comprising an effective amount of compound of claim 2, or pharmaceutically acceptable salt thereof, in association with a pharmaceutically acceptable carrier or diluent.

* * * * *